(12) United States Patent
Chervitz et al.

(10) Patent No.: US 8,764,801 B2
(45) Date of Patent: Jul. 1, 2014

(54) FACET JOINT IMPLANT CROSSLINKING APPARATUS AND METHOD

(75) Inventors: Alan Chervitz, Palm Harbor, FL (US); Daniel J. Triplett, Providence, UT (US)

(73) Assignee: Gmedelaware 2 LLC, Audubon, PA (US)

(*) Notice: Subject to any disclaimer, the term of this patent is extended or adjusted under 35 U.S.C. 154(b) by 767 days.

(21) Appl. No.: 11/350,179

(22) Filed: Feb. 7, 2006

(65) Prior Publication Data

US 2006/0217718 A1    Sep. 28, 2006

Related U.S. Application Data

(60) Provisional application No. 60/666,201, filed on Mar. 28, 2005.

(51) Int. Cl.
*A61B 17/70*        (2006.01)

(52) U.S. Cl.
USPC .......................................................... 606/247

(58) Field of Classification Search
USPC .......................... 606/61, 247, 250–253, 258; 623/17.11–17.16
See application file for complete search history.

(56) References Cited

U.S. PATENT DOCUMENTS

| | | |
|---|---|---|
| 2,677,369 A | 5/1954 | Knowles |
| 3,247,000 A | 4/1966 | Taylor |
| 3,298,372 A | 1/1967 | Feinberg |
| 3,426,364 A | 2/1969 | Lumb |
| 3,486,505 A | 12/1969 | Morrison |
| 3,508,954 A | 4/1970 | White et al. |
| 3,648,691 A | 3/1972 | Lumb et al. |
| 3,857,642 A | 12/1974 | Miller |
| 3,867,728 A | 2/1975 | Stubstad et al. |
| 3,875,595 A | 4/1975 | Froning |
| 4,003,376 A | 1/1977 | McKay |
| 4,092,078 A | 5/1978 | Klotz et al. |
| 4,289,123 A | 9/1981 | Dunn |

(Continued)

FOREIGN PATENT DOCUMENTS

| | | |
|---|---|---|
| EP | 408489 A1 | 1/1991 |
| EP | 322334 B1 | 2/1992 |

(Continued)

OTHER PUBLICATIONS

Goh JC, et al., "Influence of PLIF cage size on lumbar spine stability", Spine, Jan. 2000 25:1, PubMed abstract.

(Continued)

*Primary Examiner* — Michael T Schaper

(57) ABSTRACT

A crosslink is provided for securing orthopedic implants, such as facet joint replacement implants, together. The crosslink has a pair of implant coupling components, a pair of rod coupling components, a rod, and a pair of fasteners. Each facet joint implant may include a semicylindrical interface received in a resilient member of the corresponding implant coupling component to permit relative cephalad/caudal adjustment between the crosslink and the implants. The resilient members grip the semicylindrical interface of the implant to enable at least temporary attachment of the implant coupling components to the implants independently of the rod. Clocking features on the semicylindrical interfaces and on the interfacing areas of the implant coupling components and rod coupling components may limit assembly of the crosslink to discrete relative orientations and prevent play after assembly. The fasteners secure the rod coupling components to the rod at the desired positions along the rod.

33 Claims, 5 Drawing Sheets

(56) References Cited

U.S. PATENT DOCUMENTS

| | | | |
|---|---|---|---|
| 4,349,921 A | 9/1982 | Kuntz | |
| 4,369,769 A | 1/1983 | Edwards | |
| 4,479,491 A | 10/1984 | Martin | |
| 4,483,334 A | 11/1984 | Murray | |
| 4,501,269 A | 2/1985 | Bagby | |
| 4,554,914 A | 11/1985 | Kapp et al. | |
| 4,599,086 A | 7/1986 | Doty | |
| 4,604,995 A | 8/1986 | Stephens et al. | |
| 4,611,581 A | 9/1986 | Steffee | |
| 4,641,636 A | 2/1987 | Cotrel | |
| 4,653,481 A | 3/1987 | Howland et al. | |
| 4,657,550 A | 4/1987 | Daher | |
| 4,696,290 A | 9/1987 | Steffee | |
| 4,743,260 A | 5/1988 | Burton | |
| 4,759,769 A | 7/1988 | Hedman et al. | |
| 4,772,287 A | 9/1988 | Ray et al. | |
| 4,790,303 A | 12/1988 | Steffee | |
| 4,800,874 A | 1/1989 | David et al. | |
| 4,805,602 A | 2/1989 | Puno et al. | |
| 4,827,918 A | 5/1989 | Olerud | |
| 4,863,476 A | 9/1989 | Shepperd | |
| 4,863,477 A | 9/1989 | Monson | |
| 4,892,545 A | 1/1990 | Day et al. | |
| 4,904,260 A | 2/1990 | Ray et al. | |
| 4,911,718 A | 3/1990 | Lee et al. | |
| 4,946,458 A | 8/1990 | Harms et al. | |
| 4,955,908 A | 9/1990 | Frey et al. | |
| 5,011,484 A | 4/1991 | Breard | |
| 5,015,255 A | 5/1991 | Kuslich | |
| 5,047,055 A | 9/1991 | Bao et al. | |
| 5,071,437 A | 12/1991 | Steffee | |
| 5,092,866 A | 3/1992 | Breard et al. | |
| 5,092,867 A | 3/1992 | Harms et al. | |
| 5,092,893 A | 3/1992 | Smith | |
| 5,127,912 A | 7/1992 | Ray et al. | |
| 5,129,900 A | 7/1992 | Asher et al. | |
| 5,147,361 A | 9/1992 | Ojima et al. | |
| 5,147,404 A | 9/1992 | Downey | |
| 5,171,279 A | 12/1992 | Mathews | |
| 5,171,280 A | 12/1992 | Baumgartner | |
| 5,180,393 A | 1/1993 | Commarmond | |
| 5,192,326 A | 3/1993 | Bao et al. | |
| 5,236,460 A | 8/1993 | Barber | |
| 5,246,458 A | 9/1993 | Graham | |
| 5,258,031 A | 11/1993 | Salib et al. | |
| 5,261,910 A | 11/1993 | Warden et al. | |
| 5,263,953 A | 11/1993 | Bagby | |
| 5,276,502 A * | 1/1994 | Ohi | 356/513 |
| 5,282,863 A | 2/1994 | Burton | |
| 5,304,178 A | 4/1994 | Stahurski | |
| 5,306,275 A | 4/1994 | Bryan | |
| 5,306,308 A | 4/1994 | Gross et al. | |
| 5,306,309 A | 4/1994 | Wagner et al. | |
| 5,313,962 A | 5/1994 | Obenchain | |
| 5,318,567 A | 6/1994 | Vichard | |
| 5,360,430 A | 11/1994 | Lin | |
| 5,366,455 A | 11/1994 | Dove et al. | |
| 5,370,697 A | 12/1994 | Baumgartner | |
| 5,375,823 A | 12/1994 | Navas | |
| 5,387,213 A | 2/1995 | Breard et al. | |
| 5,391,168 A | 2/1995 | Sanders et al. | |
| 5,401,269 A | 3/1995 | Buttner-Janz et al. | |
| 5,415,661 A | 5/1995 | Holmes | |
| 5,437,669 A | 8/1995 | Yuan et al. | |
| 5,437,672 A | 8/1995 | Alleyne | |
| 5,439,464 A | 8/1995 | Shapiro | |
| 5,443,516 A | 8/1995 | Albrektsson et al. | |
| 5,456,722 A | 10/1995 | McLeod et al. | |
| 5,458,641 A | 10/1995 | Ramirez Jimenez | |
| 5,458,642 A | 10/1995 | Beer et al. | |
| 5,458,643 A | 10/1995 | Oka et al. | |
| 5,464,439 A | 11/1995 | Gendler | |
| 5,470,333 A | 11/1995 | Ray | |
| 5,476,463 A | 12/1995 | Boachie-Adjei et al. | |
| 5,480,401 A | 1/1996 | Navas | |
| 5,489,308 A | 2/1996 | Kuslich et al. | |
| 5,496,318 A | 3/1996 | Howland et al. | |
| 5,507,745 A | 4/1996 | Logroscino et al. | |
| 5,507,813 A | 4/1996 | Dowd et al. | |
| 5,514,180 A | 5/1996 | Heggeness et al. | |
| 5,522,899 A | 6/1996 | Michelson | |
| 5,527,312 A | 6/1996 | Ray | |
| 5,531,745 A | 7/1996 | Ray | |
| 5,531,747 A * | 7/1996 | Ray | 606/278 |
| 5,534,028 A | 7/1996 | Bao et al. | |
| 5,534,030 A | 7/1996 | Navarro et al. | |
| 5,534,031 A | 7/1996 | Matsuzaki et al. | |
| 5,540,688 A | 7/1996 | Navas | |
| 5,545,166 A | 8/1996 | Howland | |
| 5,545,229 A | 8/1996 | Parsons et al. | |
| 5,549,607 A * | 8/1996 | Olson et al. | 606/251 |
| 5,556,431 A | 9/1996 | Buttner-Janz | |
| 5,556,687 A | 9/1996 | McMillin | |
| 5,562,735 A | 10/1996 | Margulies | |
| 5,562,736 A | 10/1996 | Ray et al. | |
| 5,562,737 A | 10/1996 | Graf | |
| 5,569,248 A | 10/1996 | Mathews | |
| 5,571,189 A | 11/1996 | Kuslich | |
| 5,571,191 A | 11/1996 | Fitz | |
| 5,572,191 A | 11/1996 | Lundberg | |
| 5,582,612 A | 12/1996 | Lin | |
| 5,584,832 A | 12/1996 | Schlapfer | |
| 5,603,713 A | 2/1997 | Aust et al. | |
| 5,609,634 A | 3/1997 | Voydeville | |
| 5,645,597 A | 7/1997 | Krapiva | |
| 5,645,599 A | 7/1997 | Samani | |
| 5,649,926 A | 7/1997 | Howland | |
| 5,653,762 A | 8/1997 | Pisharodi | |
| 5,666,243 A | 9/1997 | Brent | |
| 5,672,175 A | 9/1997 | Martin | |
| 5,674,295 A | 10/1997 | Ray et al. | |
| 5,674,296 A | 10/1997 | Bryan | |
| 5,676,701 A | 10/1997 | Yuan et al. | |
| 5,681,310 A | 10/1997 | Yuan et al. | |
| 5,683,464 A | 11/1997 | Wagner et al. | |
| 5,683,465 A | 11/1997 | Shinn et al. | |
| 5,688,272 A * | 11/1997 | Montague et al. | 606/252 |
| 5,690,629 A | 11/1997 | Asher et al. | |
| 5,702,392 A | 12/1997 | Wu et al. | |
| 5,702,450 A | 12/1997 | Bisserie | |
| 5,702,453 A | 12/1997 | Rabbe et al. | |
| 5,704,936 A | 1/1998 | Mazel | |
| 5,713,900 A | 2/1998 | Benzel et al. | |
| 5,716,415 A | 2/1998 | Steffee | |
| 5,725,582 A | 3/1998 | Bevan et al. | |
| 5,728,097 A | 3/1998 | Mathews | |
| 5,735,899 A | 4/1998 | Schwartz et al. | |
| 5,749,873 A | 5/1998 | Fairley | |
| 5,755,796 A | 5/1998 | Ibo et al. | |
| 5,772,661 A | 6/1998 | Michelson | |
| 5,797,909 A | 8/1998 | Michelson | |
| 5,814,046 A | 9/1998 | Hopf | |
| 5,824,093 A | 10/1998 | Ray et al. | |
| 5,824,094 A | 10/1998 | Serhan et al. | |
| 5,836,948 A | 11/1998 | Zucherman et al. | |
| 5,860,977 A | 1/1999 | Zucherman et al. | |
| 5,865,846 A | 2/1999 | Bryan et al. | |
| 5,868,745 A | 2/1999 | Alleyne | |
| 5,876,404 A | 3/1999 | Zucherman et al. | |
| 5,888,223 A | 3/1999 | Bray, Jr. | |
| 5,893,889 A | 4/1999 | Harrington | |
| RE36,221 E | 6/1999 | Breard et al. | |
| 5,916,267 A | 6/1999 | Tienboon | |
| 5,951,555 A | 9/1999 | Rehak et al. | |
| 5,961,516 A | 10/1999 | Graf | |
| 5,986,169 A | 11/1999 | Gjunter | |
| 6,001,130 A | 12/1999 | Bryan et al. | |
| 6,004,322 A * | 12/1999 | Bernstein | 606/305 |
| 6,014,588 A | 1/2000 | Fitz | |
| 6,019,759 A * | 2/2000 | Rogozinski | 606/308 |
| 6,019,792 A | 2/2000 | Cauthen | |
| 6,039,761 A | 3/2000 | Li et al. | |
| 6,039,763 A | 3/2000 | Shelokov | |
| 6,048,342 A | 4/2000 | Zucherman et al. | |

(56) References Cited

U.S. PATENT DOCUMENTS

| | | | |
|---|---|---|---|
| 6,063,088 A | 5/2000 | Winslow | |
| 6,063,121 A | 5/2000 | Xavier et al. | |
| 6,066,325 A | 5/2000 | Wallace et al. | |
| 6,068,630 A | 5/2000 | Zucherman et al. | |
| RE36,758 E | 6/2000 | Fitz | |
| 6,074,390 A | 6/2000 | Zucherman et al. | |
| 6,080,157 A | 6/2000 | Cathro et al. | |
| 6,090,112 A | 7/2000 | Zucherman et al. | |
| 6,093,205 A | 7/2000 | McLeod et al. | |
| 6,113,637 A | 9/2000 | Gill et al. | |
| 6,113,639 A | 9/2000 | Ray et al. | |
| 6,132,464 A | 10/2000 | Martin | |
| 6,132,465 A | 10/2000 | Ray et al. | |
| 6,146,421 A | 11/2000 | Gordon et al. | |
| 6,149,652 A | 11/2000 | Zucherman et al. | |
| 6,151,934 A | 11/2000 | Chong et al. | |
| 6,152,926 A | 11/2000 | Zucherman et al. | |
| 6,156,038 A | 12/2000 | Zucherman et al. | |
| 6,156,067 A | 12/2000 | Bryan et al. | |
| 6,176,861 B1* | 1/2001 | Bernstein et al. | 606/246 |
| 6,179,838 B1* | 1/2001 | Fiz | 606/278 |
| 6,183,471 B1 | 2/2001 | Zucherman et al. | |
| 6,189,422 B1 | 2/2001 | Stihl | |
| 6,190,387 B1 | 2/2001 | Zucherman et al. | |
| 6,190,414 B1 | 2/2001 | Young et al. | |
| 6,206,882 B1 | 3/2001 | Cohen | |
| 6,206,922 B1 | 3/2001 | Zdeblick et al. | |
| 6,228,118 B1 | 5/2001 | Gordon | |
| 6,235,030 B1 | 5/2001 | Zucherman et al. | |
| 6,238,397 B1 | 5/2001 | Zucherman et al. | |
| 6,241,730 B1 | 6/2001 | Alby | |
| 6,264,655 B1 | 7/2001 | Pisharodi | |
| 6,267,764 B1 | 7/2001 | Elberg | |
| 6,280,444 B1 | 8/2001 | Zucherman et al. | |
| 6,290,700 B1 | 9/2001 | Schmotzer | |
| 6,293,949 B1 | 9/2001 | Justis et al. | |
| 6,312,469 B1 | 11/2001 | Gielen et al. | |
| 6,314,325 B1 | 11/2001 | Fitz | |
| 6,332,882 B1 | 12/2001 | Zucherman et al. | |
| 6,332,883 B1 | 12/2001 | Zucherman et al. | |
| 6,379,355 B1* | 4/2002 | Zucherman et al. | 606/249 |
| 6,402,750 B1 | 6/2002 | Atkinson et al. | |
| 6,413,259 B1 | 7/2002 | Lyons et al. | |
| 6,419,676 B1 | 7/2002 | Zucherman et al. | |
| 6,419,677 B2 | 7/2002 | Zucherman et al. | |
| 6,419,703 B1 | 7/2002 | Fallin et al. | |
| 6,419,704 B1 | 7/2002 | Ferree | |
| 6,440,169 B1 | 8/2002 | Elberg et al. | |
| 6,447,546 B1 | 9/2002 | Bramlet et al. | |
| 6,451,019 B1 | 9/2002 | Zucherman et al. | |
| 6,451,020 B1 | 9/2002 | Zucherman et al. | |
| 6,458,131 B1 | 10/2002 | Ray | |
| 6,461,359 B1 | 10/2002 | Tribus et al. | |
| 6,471,704 B2* | 10/2002 | Gertzbein et al. | 606/250 |
| 6,475,219 B1 | 11/2002 | Shelokov | |
| 6,478,796 B2 | 11/2002 | Zucherman et al. | |
| 6,481,440 B2 | 11/2002 | Gielen et al. | |
| 6,485,518 B1 | 11/2002 | Cornwall et al. | |
| 6,500,178 B2 | 12/2002 | Zucherman et al. | |
| 6,514,256 B2 | 2/2003 | Zucherman et al. | |
| 6,527,806 B2 | 3/2003 | Ralph et al. | |
| 6,540,747 B1 | 4/2003 | Marino | |
| 6,540,785 B1 | 4/2003 | Gill et al. | |
| 6,565,605 B2 | 5/2003 | Goble et al. | |
| 6,579,319 B2 | 6/2003 | Goble et al. | |
| 6,582,433 B2* | 6/2003 | Yun | 606/249 |
| 6,585,769 B1 | 7/2003 | Muhanna et al. | |
| 6,610,091 B1 | 8/2003 | Reiley | |
| 6,616,669 B2 | 9/2003 | Ogilvie et al. | |
| 6,626,909 B2 | 9/2003 | Chin | |
| 6,626,944 B1 | 9/2003 | Taylor | |
| 6,652,527 B2 | 11/2003 | Zucherman et al. | |
| 6,652,534 B2 | 11/2003 | Zucherman et al. | |
| 6,652,585 B2 | 11/2003 | Lange | |
| 6,669,729 B2 | 12/2003 | Chin | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,733,534 B2 | 5/2004 | Sherman | |
| 6,761,719 B2 | 7/2004 | Justis et al. | |
| 6,761,720 B1 | 7/2004 | Senegas | |
| 6,783,527 B2 | 8/2004 | Drewry et al. | |
| 6,796,983 B1 | 9/2004 | Zucherman et al. | |
| 6,811,567 B2 | 11/2004 | Reiley | |
| 6,835,205 B2 | 12/2004 | Atkinson et al. | |
| 6,835,207 B2 | 12/2004 | Zacouto et al. | |
| 2001/0007073 A1 | 7/2001 | Zucherman et al. | |
| 2001/0012938 A1 | 8/2001 | Zucherman et al. | |
| 2001/0016743 A1 | 8/2001 | Zucherman et al. | |
| 2001/0021850 A1 | 9/2001 | Zucherman et al. | |
| 2001/0031965 A1 | 10/2001 | Zucherman et al. | |
| 2001/0039452 A1 | 11/2001 | Zucherman et al. | |
| 2002/0029039 A1* | 3/2002 | Zucherman et al. | 606/61 |
| 2002/0065557 A1 | 5/2002 | Goble et al. | |
| 2002/0072800 A1 | 6/2002 | Goble et al. | |
| 2002/0091446 A1 | 7/2002 | Zucherman et al. | |
| 2002/0099384 A1 | 7/2002 | Scribner et al. | |
| 2002/0116000 A1 | 8/2002 | Zucherman et al. | |
| 2002/0123806 A1 | 9/2002 | Reiley | |
| 2002/0143331 A1 | 10/2002 | Zucherman et al. | |
| 2002/0151895 A1 | 10/2002 | Soboleski et al. | |
| 2002/0183746 A1 | 12/2002 | Zucherman et al. | |
| 2003/0004572 A1 | 1/2003 | Goble et al. | |
| 2003/0009226 A1 | 1/2003 | Graf | |
| 2003/0028250 A1* | 2/2003 | Reiley et al. | 623/17.11 |
| 2003/0040797 A1 | 2/2003 | Fallin et al. | |
| 2003/0055427 A1 | 3/2003 | Graf | |
| 2003/0065330 A1 | 4/2003 | Zucherman et al. | |
| 2003/0073998 A1* | 4/2003 | Pagliuca et al. | 606/61 |
| 2003/0109880 A1 | 6/2003 | Shirado et al. | |
| 2003/0153912 A1 | 8/2003 | Graf | |
| 2003/0191470 A1 | 10/2003 | Ritland | |
| 2003/0212398 A1* | 11/2003 | Jackson | 606/61 |
| 2003/0220642 A1 | 11/2003 | Freudiger | |
| 2003/0220643 A1 | 11/2003 | Ferree | |
| 2004/0006341 A1 | 1/2004 | Shaolian et al. | |
| 2004/0006343 A1* | 1/2004 | Sevrain | 606/61 |
| 2004/0006391 A1* | 1/2004 | Reiley | 623/17.11 |
| 2004/0024458 A1 | 2/2004 | Senegas et al. | |
| 2004/0049189 A1 | 3/2004 | Le Couedic et al. | |
| 2004/0049190 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0073215 A1 | 4/2004 | Carli | |
| 2004/0078082 A1 | 4/2004 | Lange | |
| 2004/0082954 A1 | 4/2004 | Teitelbaum et al. | |
| 2004/0087950 A1 | 5/2004 | Teitelbaum | |
| 2004/0106995 A1 | 6/2004 | Le Couedic et al. | |
| 2004/0111154 A1 | 6/2004 | Reiley | |
| 2004/0116927 A1 | 6/2004 | Graf | |
| 2004/0117017 A1 | 6/2004 | Pasquet et al. | |
| 2004/0127989 A1 | 7/2004 | Dooris et al. | |
| 2004/0133203 A1* | 7/2004 | Young et al. | 606/61 |
| 2004/0143264 A1 | 7/2004 | McAfee | |
| 2004/0147928 A1* | 7/2004 | Landry et al. | 606/61 |
| 2004/0153071 A1 | 8/2004 | Zucherman et al. | |
| 2004/0158245 A1* | 8/2004 | Chin | 606/61 |
| 2004/0167520 A1 | 8/2004 | Zucherman et al. | |
| 2004/0172025 A1 | 9/2004 | Drewry et al. | |
| 2004/0181282 A1 | 9/2004 | Zucherman et al. | |
| 2004/0181285 A1 | 9/2004 | Simonson | |
| 2004/0186475 A1 | 9/2004 | Falahee | |
| 2004/0220568 A1 | 11/2004 | Zucherman et al. | |
| 2004/0225289 A1 | 11/2004 | Biedermann et al. | |
| 2004/0230192 A1 | 11/2004 | Graf | |
| 2004/0230201 A1 | 11/2004 | Yuan et al. | |
| 2004/0230304 A1* | 11/2004 | Yuan et al. | 623/17.11 |
| 2004/0236327 A1 | 11/2004 | Paul et al. | |

(56) References Cited

U.S. PATENT DOCUMENTS

| | | |
|---|---|---|
| 2004/0236328 A1 | 11/2004 | Paul et al. |
| 2004/0236329 A1 | 11/2004 | Panjabi |
| 2004/0243239 A1 | 12/2004 | Taylor |
| 2005/0010291 A1* | 1/2005 | Stinson et al. ............ 623/17.11 |
| 2005/0010293 A1 | 1/2005 | Zucherman et al. |
| 2005/0010298 A1 | 1/2005 | Zucherman et al. |
| 2005/0027361 A1 | 2/2005 | Reiley |
| 2005/0043797 A1 | 2/2005 | Lee |
| 2005/0043799 A1 | 2/2005 | Reiley |
| 2005/0070899 A1 | 3/2005 | Doubler |
| 2005/0119748 A1* | 6/2005 | Reiley et al. ............. 623/17.11 |
| 2005/0131406 A1 | 6/2005 | Reiley et al. |
| 2005/0137705 A1 | 6/2005 | Reiley |
| 2005/0137706 A1 | 6/2005 | Reiley |
| 2005/0143818 A1* | 6/2005 | Yuan et al. ............... 623/17.11 |
| 2005/0149190 A1* | 7/2005 | Reiley ...................... 623/17.11 |
| 2005/0154467 A1 | 7/2005 | Peterman et al. |
| 2005/0177166 A1 | 8/2005 | Timm |
| 2005/0228400 A1 | 10/2005 | Chao et al. |
| 2005/0240266 A1* | 10/2005 | Kuiper et al. ............ 623/17.11 |
| 2006/0079903 A1 | 4/2006 | Wong |
| 2006/0217718 A1 | 9/2006 | Chervitz |
| 2008/0200918 A1 | 8/2008 | Spitler et al. |
| 2008/0282846 A1 | 11/2008 | Sharifi-Mehr et al. |
| 2009/0163963 A1 | 6/2009 | Berrevoets |

FOREIGN PATENT DOCUMENTS

| | | |
|---|---|---|
| EP | 667127 A1 | 8/1995 |
| EP | 767637 B1 | 11/1998 |
| EP | 768843 B1 | 2/1999 |
| EP | 669109 B1 | 5/1999 |
| EP | 1239785 B1 | 9/2004 |
| EP | 1343424 B1 | 9/2004 |
| EP | 1399078 B1 | 12/2004 |
| FR | 2721501 B1 | 8/1996 |
| JP | 10179622 A2 | 7/1998 |
| JP | 10277070 A2 | 10/1998 |
| SU | 1468543 A1 | 3/1989 |
| SU | 1517953 A1 | 10/1989 |
| WO | WO8707827 A1 | 12/1987 |
| WO | WO9421185 A1 | 9/1994 |
| WO | WO9505783 A1 | 3/1995 |
| WO | WO9505784 A1 | 3/1995 |
| WO | WO9505785 A1 | 3/1995 |
| WO | WO9505786 A1 | 3/1995 |
| WO | WO9600049 A1 | 1/1996 |
| WO | WO9822033 A1 | 5/1998 |
| WO | WO9848707 A1 | 11/1998 |
| WO | WO9848717 A1 | 11/1998 |
| WO | WO9856301 A1 | 12/1998 |
| WO | WO9905995 A1 | 2/1999 |
| WO | WO9921500 A1 | 5/1999 |
| WO | WO9921501 A1 | 5/1999 |
| WO | WO9923963 A1 | 5/1999 |
| WO | WO9965412 A1 | 12/1999 |
| WO | WO9960957 C2 | 5/2000 |
| WO | WO0038582 | 7/2000 |
| WO | WO0062684 A1 | 10/2000 |
| WO | WO0130248 A1 | 5/2001 |
| WO | WO0145576 A1 | 6/2001 |
| WO | WO0149192 A1 | 7/2001 |
| WO | WO0156489 A1 | 8/2001 |
| WO | WO0164142 A1 | 9/2001 |
| WO | WO0164144 A2 | 9/2001 |
| WO | WO0191657 A1 | 12/2001 |
| WO | WO0191658 A1 | 12/2001 |
| WO | WO0197721 A2 | 12/2001 |
| WO | WO0197721 A3 | 12/2001 |
| WO | WO0200124 A1 | 1/2002 |
| WO | WO0203882 A2 | 1/2002 |
| WO | WO0207621 A1 | 1/2002 |
| WO | WO0207622 A1 | 1/2002 |
| WO | WO0207623 A1 | 1/2002 |
| WO | WO0213732 A3 | 2/2002 |
| WO | WO0230336 A2 | 4/2002 |
| WO | WO0234120 A2 | 5/2002 |
| WO | WO0243603 A1 | 6/2002 |
| WO | WO02067792 A2 | 9/2002 |
| WO | WO02067793 A2 | 9/2002 |
| WO | WO02089712 A1 | 11/2002 |
| WO | WO02089712 A2 | 11/2002 |
| WO | WO02102259 A2 | 12/2002 |
| WO | WO03009737 A1 | 2/2003 |
| WO | WO03011147 A1 | 2/2003 |
| WO | WO03015646 A2 | 2/2003 |
| WO | WO03045262 A2 | 6/2003 |
| WO | WO03077806 A1 | 9/2003 |
| WO | WO2004017817 A2 | 3/2004 |
| WO | WO2004019762 A2 | 3/2004 |
| WO | WO2004024010 A1 | 3/2004 |
| WO | WO2004032794 A2 | 4/2004 |
| WO | WO2004032794 A3 | 4/2004 |
| WO | WO2004039239 A2 | 5/2004 |
| WO | WO2004039239 A3 | 5/2004 |
| WO | WO2004039243 A2 | 5/2004 |
| WO | WO2004039243 A3 | 5/2004 |
| WO | WO2004041066 A2 | 5/2004 |
| WO | WO2004041066 A3 | 5/2004 |
| WO | WO2004073533 A2 | 9/2004 |
| WO | WO2004098423 A1 | 11/2004 |
| WO | WO2004098452 A2 | 11/2004 |
| WO | WO2004105577 A2 | 12/2004 |
| WO | WO2004105580 A2 | 12/2004 |
| WO | WO2005013864 | 2/2005 |
| WO | WO2005037149 | 4/2005 |
| WO | WO2005044152 A1 | 5/2005 |

OTHER PUBLICATIONS

Head WC, Wagner surface replacement arthroplasty of the hip. Analysis of fourteen failures in forty-one hips:, J Bone Joint Surg. [Am], Mar. 1981 63:3, PubMed Abstract.

Kotani Y, et al., "The effects of spinal fixation and destabilization on the biomechanical and histologic properties of spinal ligaments. An in vivo study.", Spine, Mar. 15, 1998 23:6, PubMed abstract.

Lemaire JP, et al., "Intervertebral Disc Prosthesis: Results and Prospects for the Year 2000", Clinical Orthopaedics and Related Research, PubMed abstract.

Nagata H, et al., "The effects of immobilization of long segments of the spine on the adjacent and distal facet force and lumbrosacral motion", Spine Dec. 1993 18:16. PubMed abstract.

Nibu K, et al., Multidirectional stabilizing potential of BAK interbody spinal fusion system for anterior surgery, J Spinal Discord, Aug. 1997 10:4, PubMed abstract.

Tsantrizos A, et al., "Segmental stability and compressive strength of posterior lumbar interbody fusion implants", Spine, Aug. 1, 2000 25:15, PubMed abstract.

Todd Anres; *Facet Joint Arthroplasty: A Glimpse of the Future of Spine Technology*, Othopaedic Product News, Sep./Oct. 2005 p. 38,40.

IPRP and Written Opinion in matter PCT/US2009/066761.

ISR in matter PCT/US2009/066761.

* cited by examiner

FACET JOINT IMPLANT CROSSLINKING APPARATUS AND METHOD

CROSS-REFERENCE TO RELATED APPLICATIONS

This application claims the benefit of the following:
U.S. Provisional Patent Application Ser. No. 60/666,201 filed Mar. 28, 2005 and is entitled FACET JOINT IMPLANT CROSSLINKING APPARATUS AND METHOD.

BACKGROUND OF THE INVENTION

1. The Field of the Invention

The present invention relates generally to systems and methods for securing orthopedic implants, and more specifically, to facet joint replacement implant crosslinking systems.

2. The Relevant Technology

Orthopedic medicine provides a wide array of implants that can be attached to bone to alleviate various pathologies. One unique challenge in orthopedics is the stabilization of implants that bear loads. For example, it has been proposed to use implants to replace the articulating surfaces of facet joints of the spine. Such articulating surfaces are subject to not only sliding articulation, but also direct pressure induced by rotation or lateral bending of the spine. Accordingly, in order to remain in their proper positions, such implants must be firmly anchored to bone. Such anchoring is particularly challenging in the spine, where there is limited bone mass available to receive fasteners.

Accordingly, there is a need for systems capable of more securely attaching implants to bone. More particularly, there is a need for such systems that do not require a large quantity of bone mass for anchoring, are easily installed in surgery, and are compatible with known minimally invasive surgical methods. Furthermore, there is a need for such systems that are capable of providing a discretely adjustable displacement between cooperating implants, and are adjustably positionable with respect to the implants they stabilize.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to stabilize orthopedic implants such as facet joint replacement implants. The present invention simplifies the installation and configuration of facet joint replacement systems, and enhances their longevity and reliability. The configuration and operation of various embodiments of the invention will be shown and described in greater detail with reference to FIGS. 1 through 5, as follows.

Figure 1:
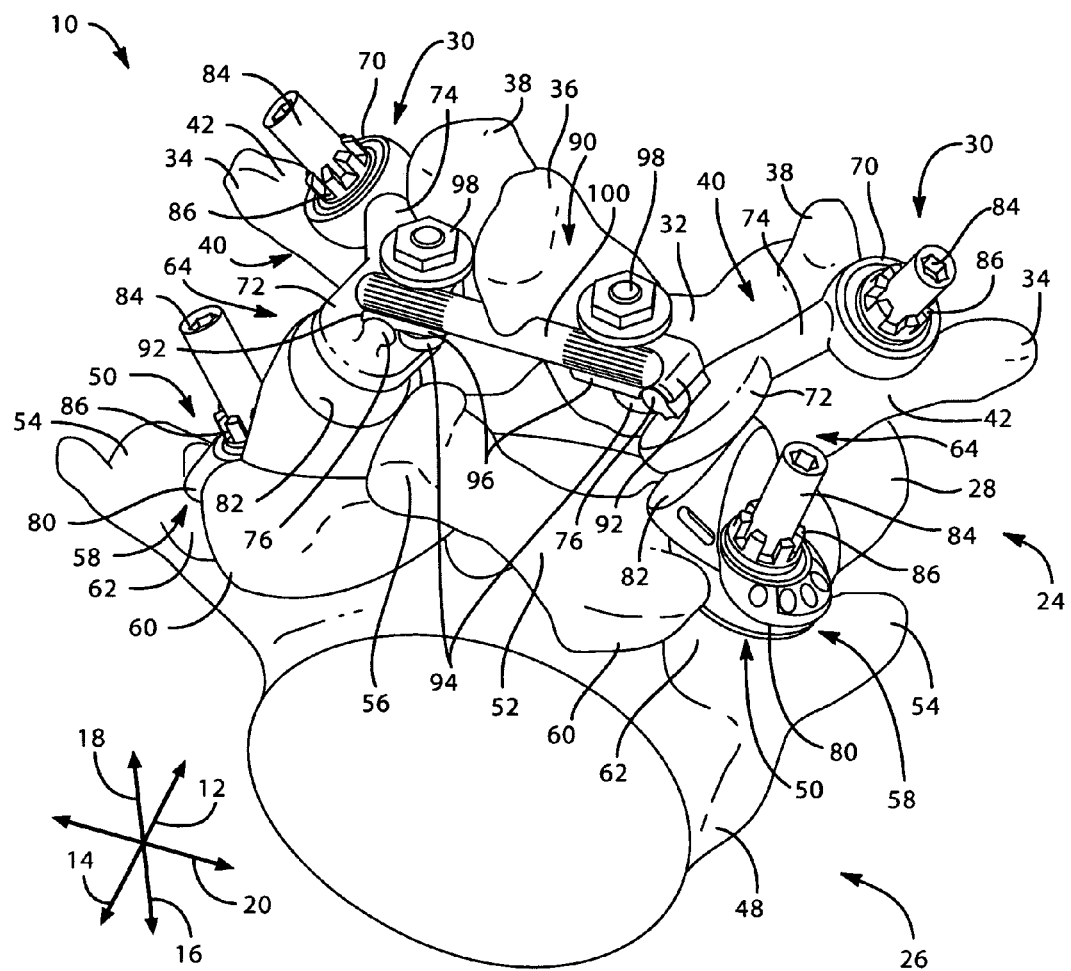
FIG. 1 is a caudal, perspective view of the L4 and L5 vertebrae of a spinal column, with an apparatus according to one embodiment of the invention attached to stabilize a pair of inferior facet implants of the superior vertebra.

Referring to FIG. 1, a caudal, perspective view illustrates a portion of a spine 10. FIG. 1 illustrates only the bony structures; accordingly, ligaments, cartilage, and other soft tissues are omitted for clarity. The spine 10 has a cephalad direction 12, a caudal direction 14, an anterior direction 16, a posterior direction 18, and a medial/lateral axis 20, all of which are oriented as shown by the arrows bearing the same reference numerals. In this application, "left" and "right" are used with reference to a posterior view, i.e., a view from behind the spine 10. "Medial" refers to a position or orientation toward a sagittal plane of the spine 10, and "lateral" refers to a position or orientation relatively further from the sagittal plane.

As shown, the portion of the spine 10 illustrated in FIG. 1 includes a first vertebra 24, which may be the L4 (Fourth Lumbar) vertebra of a patient, and a second vertebra 26, which may be the L5 (Fifth Lumbar) vertebra of the patient. The systems and methods may be applicable to any vertebra or vertebrae of the spine 10 and/or the sacrum (not shown). In this application, the term "vertebra" may be broadly interpreted to include the sacrum.

As shown, the first vertebra 24 has a body 28 with a generally disc-like shape and two pedicles 30 that extend posteriorly from the body 28. A posterior arch, or lamina 32, extends between the posterior ends of the pedicles 30 to couple the pedicles 30 together. The first vertebra 24 also has a pair of transverse processes 34 that extend laterally from the pedicles 30 generally along the medial/lateral axis 20, and a spinous process 36 that extends from the lamina 32 along the posterior direction 18.

The first vertebra 24 also has a pair of superior facets 38, which are positioned toward the top of the first vertebra 24 and face generally medially. The natural inferior facets (not shown) of the first vertebra 24 have been resected away, and a pair of inferior facet joint implants 40, or inferior implants 40, has been attached to the first vertebra 24 to replace the natural inferior articular surfaces. Each of the inferior implants 40 is attached to a saddle point 42 of the first vertebra 24. Each saddle point 42 is positioned generally at the center of the juncture of each superior facet 38 with the adjacent transverse process 34.

Similarly, the second vertebra 26 has a body 48 from which two pedicles 50 extend posteriorly. A posterior arch, or lamina 52, extends between the posterior ends of the pedicles 50 to couple the pedicles 50 together. The second vertebra 26 also has a pair of transverse processes 54 that extend from the pedicles 50 generally along the medial/lateral axis 20, and a spinous process 56 that extends from the lamina 52 along the posterior direction 18.

The natural superior facets (not shown) of the second vertebra 26 have been resected away, and a pair of inferior facet replacement implants 58, or inferior implants 58, has been attached to the second vertebra 26 to replace the natural superior articular surfaces. Additionally, the second vertebra 26 has inferior facets 60, which are positioned toward the bottom of the second vertebra 26 and face generally outward. Each of the superior implants 58 is attached to a saddle point 62 of the corresponding pedicle 50 of the second vertebra 26. Each saddle point 62 is positioned generally at the center of the juncture of the corresponding natural superior facet (not shown) with the adjacent transverse process 54.

The inferior implants 40 on the first vertebra 24 articulate (i.e., slide and/or press) with the superior implants 58 of the second vertebra 26 to limit relative motion between the first and second vertebrae 24, 26 in a manner similar to that of the resected natural articular surfaces. The combination of each inferior implant 40 with the adjacent superior implant 58 provides a prosthetic facet joint 64. The prosthetic facet joints 64 cooperate with an intervertebral disc 66 positioned between the vertebrae 24, 26 to limit relative motion between the vertebrae 24, 26. The superior facets 38 of the first vertebra 24 and the inferior facets 60 of the second vertebra 26 are part of natural facet joints that control motion between the first and second vertebrae 24, 26 and adjacent vertebrae (not shown).

As illustrated in FIG. 1, each of the inferior implants 40 has a mounting portion 70, an articulation portion 72, a stem 74, and a crosslink coupling feature 76. Each mounting portion 70 is shaped to be attached to the corresponding saddle point 42 of the first vertebra 24. Each articulation portion 72 is shaped to articulate with the adjacent superior implant 58 in a manner that mimics the articulation between two natural facet articular surfaces. The stem 74 of each inferior implant 40 couples the mounting portion 70 to the corresponding articulation portion 72. The crosslink coupling feature 76 extends from the articulation portion 72, and is shaped to permit relatively easy and reliable linking of the two inferior implants 40 to each other, as will be described subsequently.

Each of the superior implants 58 has a mounting portion 80 and an articulation portion 82. Each mounting portion 80 is shaped to be attached to the corresponding saddle point 62 of the second vertebra 26. Each articulation portion 82 is shaped to articulate with the articulation portion 72 of the corresponding inferior implant 40.

Each of the inferior and superior implants 40, 58 may be coupled to the corresponding saddle point 42 or 62 through the use of a fixation member such as a pedicle screw 84, and a retention member such as a castle nut 86. In FIG. 1, the pedicle screws 84 are implanted into the pedicles 30, 50 and the mounting portions 70, 80 are positioned such that the exposed proximal ends of the pedicle screws 84 pass through apertures (not shown) of the mounting portions 70, 80. The castle nuts 86 hold the mounting portions 70, 80 in place.

The articulation portions 72 of the inferior implants 40 are constrained to remain at a fixed displacement and orientation with respect to each other by an apparatus 90 according to the invention. The apparatus 90 may be termed a "crosslink" because it couples implants of a bilateral set together. The apparatus 90 of FIG. 1 has two implant coupling components 92, two bolts 94, two rod coupling components 96, two nuts 98, and a rod 100. Each implant coupling component 92 cooperates with the corresponding bolt 94 to retain the crosslink coupling feature 76 of one of the inferior implants 40. Each rod coupling component 96 cooperates with the corresponding nut 98 to retain one end of the rod 100. The configuration and operation of the various components of the apparatus 90 will be shown and described in greater detail subsequently.

The apparatus 90 serves to substantially prevent relative translation or rotation between the articulation portions 72 of the inferior implants 40. Accordingly, the inferior implants 40 combine with the apparatus 90 to define a substantially rigid structure attached at both ends to the saddle points 42 of the first vertebra 24. Such a structure is far more resistant to slippage than one attached at only one end. Accordingly, as the spine 10 moves and the superior implants 58 exert force on the inferior implants 40, the inferior implants 40 are able to remain in place with respect to the first vertebra 24 to provide optimal, natural articulation.

Figure 2:
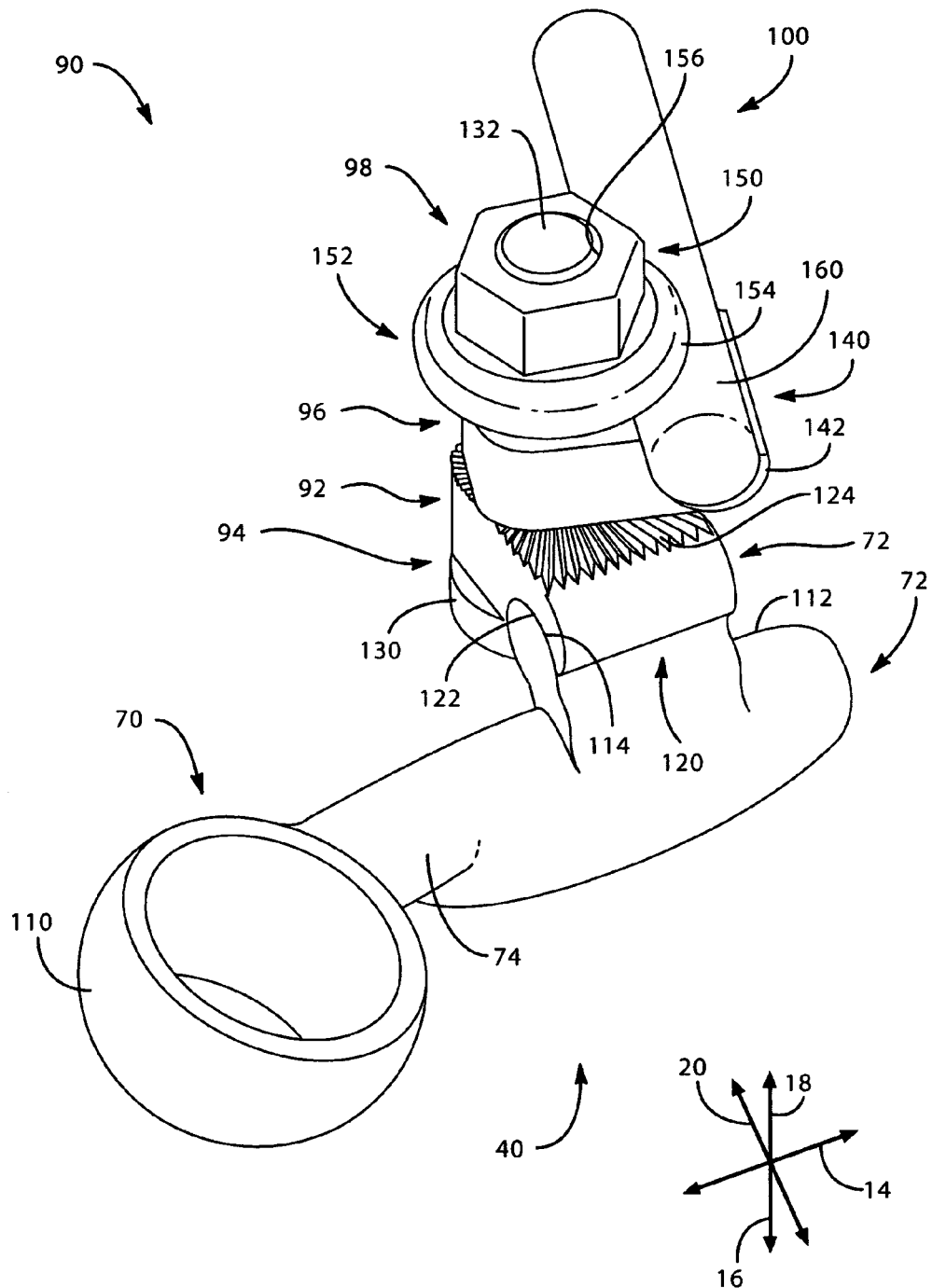
FIG. 2 is a perspective view of the left half of the apparatus of FIG. 1, along with the corresponding inferior facet implant.

Referring to FIG. 2, a perspective view illustrates the left half of the apparatus 90 in isolation. As shown, the mounting portion 70 of the inferior implant 40 has a semispherical bone apposition surface that may permit polyaxial rotation of the mounting portion 70 relative to the first vertebra 24 prior to locking of the orientation of the mounting portion 70 with the corresponding castle nut 86. The articulation portion 72 has an articular surface 112, which may have a generally convex shape. The articular surface 112 is shaped to approximate the articular surface of a natural inferior articular process. The crosslink coupling feature 76 has a semicylindrical interface 114 that facilitates attachment of the apparatus 90 to the inferior implant 40.

The implant coupling component 92 has a linking extension 120 that protrudes from the main body of the implant coupling component. The linking extension 120 has a semicylindrical interface 122 that is generally concave in shape and mates with the semicylindrical interface 114 of the corresponding crosslink coupling feature 76. If desired, the semicylindrical interfaces 122, 114 may fit relatively tightly together to restrict relative translational and rotational sliding along or about the cephalad and caudal directions 12, 14. A clocking feature (not visible in FIG. 2) may also be used to restrict relative rotation of the semicylindrical interfaces 122, 114 about the cephalad and caudal directions 12, 14.

The implant coupling component 92 also has a clocking feature 124 that is designed to restrict relative rotation between the implant coupling component 92 and the rod coupling component 96. The clocking feature 124 may take the form of a plurality of substantially ridges that extend generally radially from a bore (not shown) of the implant coupling component. The ridges cooperate with corresponding ridges (not shown) of the rod coupling component 96 to enable the implant coupling component 92 and the rod coupling component 96 to be positioned in a limited number of discrete relative orientations. The cooperation of the ridges also substantially prevents relative rotation once the implant coupling component 92 and the rod coupling component 96 are in position to abut one another, as shown in FIG. 2.

The bolt 94 has a head 130 positioned adjacent to the implant coupling component 92 and a shank 132 that passes through (or substantially through) each of the implant coupling component 92, the rod coupling component 94, and the nut 98. The head 130 protrudes in such a manner that the head is able to cooperate with the linking extension 120 to grip the associated crosslink coupling feature 76. If desired, a portion (not visible) of the head 130 that faces the linking extension 120 may have a concave radius similar to the radius of the semicylindrical interface 122 of the linking extension 120. The shank 132 is threaded to facilitate assembly of the various components 92, 94, 96, 98, 100 of the apparatus 90.

The rod coupling component 96 has a linking extension 140, which may be configured somewhat similarly to the linking extension 120 of the implant coupling component 92. More precisely, the linking extension 140 extends from a main body of the rod coupling component 96 and has a semicylindrical interface 142 with a concave shape that faces the nut 98. The semicylindrical interface 142 is sized to receive the corresponding end of the rod 100.

The nut 98 has a torque receiver 150 and a retention flange 152. The torque receiver 150 is shaped to receive torque from a tool, and therefore may have a polygonal cross sectional shape such as the hexagonal shape illustrated in FIG. 2. The torque receiver 150 facilitates tightening of the nut 98 on the end of the shank 132 of the bolt 94. The retention flange 152 may have a generally circular shape, and may have a rod retention surface 154 that is able to cooperate with the linking extension 140 of the rod coupling component 96 to grip the rod 100. The rod retention surface 154 may thus face the linking extension 140 and may have a concave radius similar to the radius of the semicylindrical interface 142 of the linking extension 140.

The nut 98 has a bore 156 through which the end of the shank 132 of the bolt 94 passes. The bore 156 has threads that mate with the threads of the shank 132 to provide threaded engagement sufficiently strong to keep the nut 98 in place after the proper torque has been applied to the nut 98.

The rod 100 has a first end 160 and a second end (not shown in FIG. 2). The first end 160 is retained by the rod coupling component 96 and the nut 98 illustrated in FIG. 2, as described previously. The second end is retained by corresponding components (not shown in FIG. 2) of the opposite side of the apparatus 90. The first end 160 and the second end may each have a clocking feature (not shown) such as a plurality of alternating, parallel ridges and grooves that mesh with corresponding grooves and ridges of the semicylindrical surface 142 of the linking extension 140 of the rod coupling component 96. The clocking feature helps to prevent relative rotation between the rod 100 and the rod coupling component 96 about the axis of the rod 100.

Advantageously, the apparatus 90 avoids interference with the lamina 32 or the spinous process 36 of the first vertebra 24. Rather, the rod 100 passes inferiorly of the spinous process 36. If desired, the apparatus 90 could be anchored to the spinous process 36 through the use of a variety of structures such as gripping plates attached to the rod 100 to grip the left and right sides of the spinous process 36. Indeed, if desired, the rod 100 may even be positioned to pass through a portion of the spinous process 36.

According to one method of assembly, the pedicle screws 84 may first be implanted in the pedicles 30, 50 of the vertebrae 24, 26, and bone beds may be formed in the saddle points 42, 62 via reaming operations or the like. Then, the inferior and superior implants 40, 58 may be positioned such that the mounting portions 70, 80 rest within the bone beds at the saddle points 42, 62. The implants 40, 58 are then oriented as desired and coupled to the saddle points 42, 62 through the use of the castle nuts 86.

After the implants 40, 58 have been secured to the vertebrae 24, 26, respectively, the apparatus 90 may be installed. The implant coupling component 92 and the bolt 94 of each side may first be positioned to retain the corresponding crosslink coupling feature 76, but left relatively loose due to the absence of the nut 98. The rod coupling component 96 and the nut 98 may then be inserted on the shank 132 of the bolt 94. Once the components 92, 94, 96, 98 for each side are in place, the rod 100 may be positioned such that the ends 160, 162 rest within the linking extensions 140 of the rod coupling components 96. Then, the nuts 98 are tightened on the shanks 132 to secure attachment to the crosslink coupling features 76 and the rod 100, thereby providing the crosslink 90 with the rigidity needed to keep the articulation portions 72 of the inferior implants 40 in place.

The apparatus 90 of FIGS. 1 and 2 is only one of many embodiments that may be used according to the invention. According to alternative embodiments, one or more of the components 92, 94, 96, 98, 100 described previously may be altered or exchanged for other components, or even combined or omitted, to provide a wide range of different crosslinking devices. According to some alternative embodiments, support struts may be used to further support the articulation portions 72 of the inferior implants 40 to prevent motion of the articulation portions in response to forces exerted along the cephalad and caudal directions 12, 14. One such support strut will be shown and described in FIG. 3, as follows.

Figure 3:
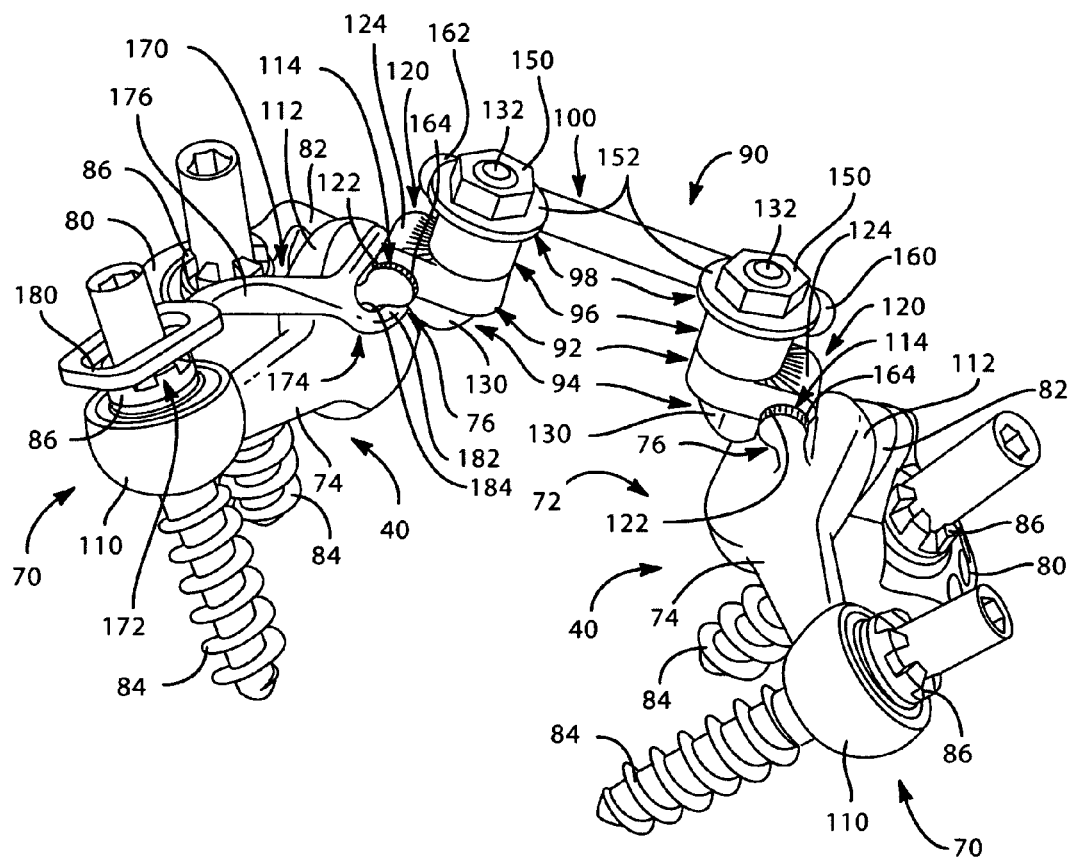
FIG. 3 is a cephalad, perspective view of the apparatus of FIG. 1, with an optional support strut.

Referring to FIG. 3, a cephalad, perspective view illustrates the inferior implants 40, the superior implants 58, the pedicle screws 84, the castle nuts 86, and the apparatus 90 in isolation, along with a support strut according to one embodiment of the invention. As shown, the rod 100 has a second end 162 that is coupled to the components 92, 94, 96, 98 of the right-hand side of the apparatus 90.

FIG. 3 also more clearly illustrates a clocking feature 164, in the form of a series of alternating parallel grooves and ridges, which may be present on the semicylindrical interfaces 114 of each of the crosslink coupling features 76. The grooves and ridges may mate with corresponding ridges and grooves of the semicylindrical surface 122 of the crosslinking extension 120 of the implant coupling component 92. As described previously, the clocking features 164 help to prevent relative rotation between each inferior implant 40 and the crosslink 90 about the cephalad and caudal directions 12, 14.

As mentioned previously, FIG. 3 also illustrates a support strut 170 according to one embodiment of the invention. The support strut 170 is coupled to extend between the pedicle screw 84 to which the right-hand inferior implant 40 is attached, and the crosslink coupling feature 76 of the right-hand inferior implant 40. In the embodiment of FIG. 3, the support strut 170 has a first end 172, a second end 174, and a stem 176 extending between the first and second ends 172, 174.

The first end 172 has a mounting slot 180 having a generally elongated shape with a width sufficient to permit insertion of the proximal end of the pedicle screw 84 therethrough. The second end 174 has a pair of tines 182 that extend generally parallel to each other to define a retention groove 184 between them. The retention groove 184 has a generally rectangular shape sized to slide around the narrowest portion of the crosslink coupling feature 76, which is the necked down portion of the crosslink coupling feature 76 adjoining the articulation portion 72 of the inferior implant 40. The stem 176 is shaped to position the first and second ends 172, 174 at their necessary relative orientations.

The support strut may be relatively easily installed by first, sliding the tines 182 on either side of the crosslink coupling feature 76, and second, inserting the mounting slot 180 over the exposed proximal end of the pedicle screw 84 to rest on the castle nut 86. A fastening element such as an additional castle nut (not shown) may be coupled to the proximal end of the pedicle screw 84 and tightened over the first end 172 so that the first end 172 is held substantially rigid with respect to the pedicle screw 84.

Once in place, the support strut 170 serves to substantially prevent rotation of the corresponding inferior implant 40 that would allow the articulation portion 72 to move along the cephalad direction 12 and the posterior direction 18. Such support is beneficial because this mode of rotation tends to be induced by articulation of the inferior and superior implants 40, 58, particularly when the spine 10 is in axial rotation. Axial rotation may cause the articulation portion 82 of the superior implant 58 to press posteriorly against the articulation portion 72 of the inferior implant 40. The support strut 170 helps to keep the articulation portion 72 in place under such a posteriorly oriented force.

The support strut 170 of FIG. 3 represents only one of many different support strut embodiments that may be used within the present invention. According to one alternative embodiment (not shown), a support strut may have a first end attached to the pedicle screw 84 used to attach the inferior implant 40 to the first vertebra 24 in a manner similar to that of the support strut 170, and a second end attached to the apparatus 90. For example, the bolt 94 of the corresponding side of the apparatus 90 may be elongated, and may pass through an aperture of the second end of the support strut. The second end of the support strut may then be secured to the bolt 94 through the use of an additional castle nut or the like. In a similar alternative embodiment, the nut 98 may be omitted in favor of use of the second end to retain the rod 100 in a manner similar to that of the retention flange 152 of the nut 98, thereby reducing the part count and profile of the implanted assembly.

According to other alternative embodiments, additional clocking features may be added to enhance the stability of the assembled crosslink. Further, alternative crosslinks may be configured to ease assembly by providing temporary connections that enable the various components to be positioned, assembled, and/or adjusted before a more permanent, rigid form of fastening is applied. One such embodiment will be shown and described in connection with FIGS. 4 and 5, as follows.

Figure 4:
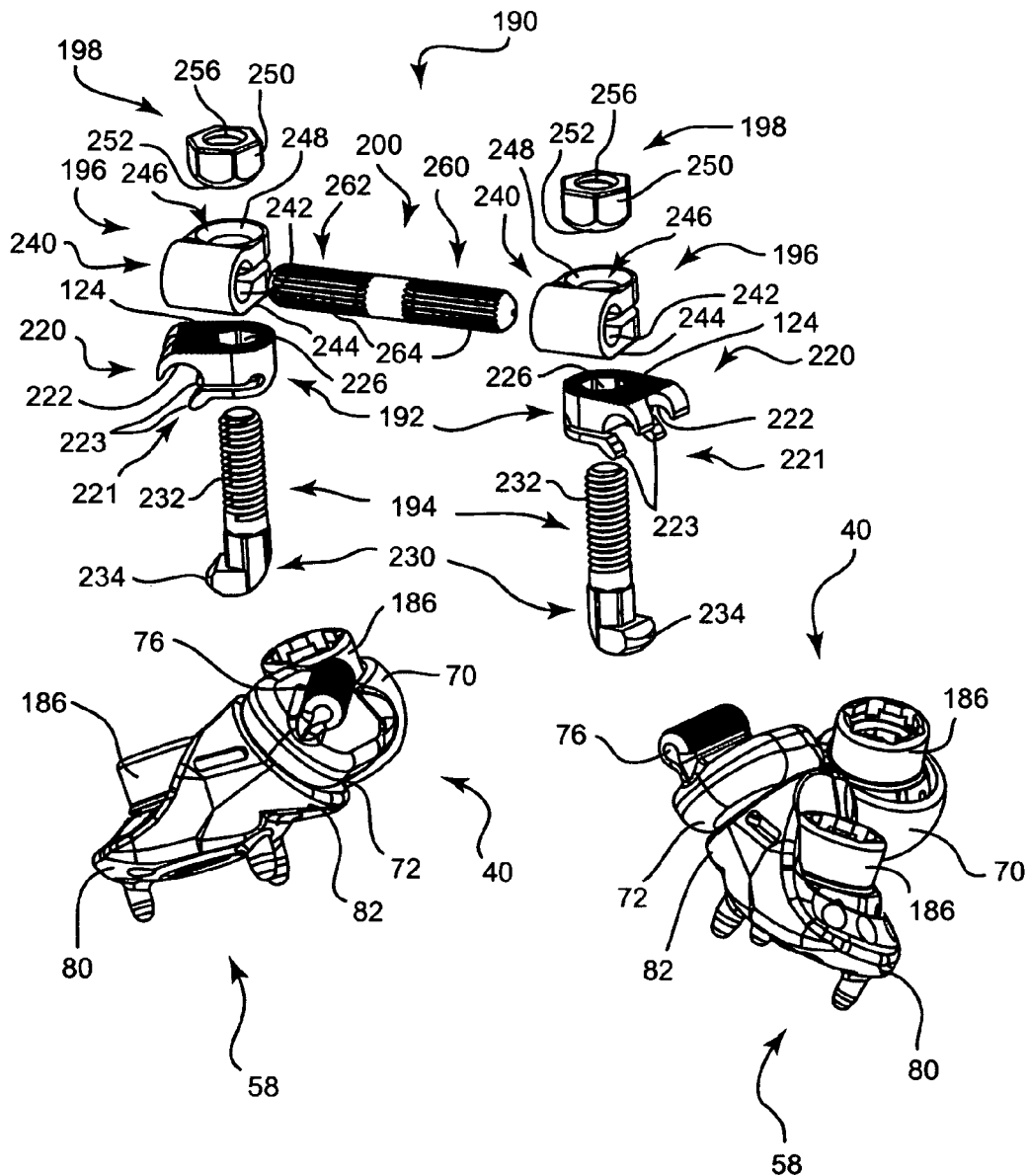
FIG. 4 is a caudal, perspective, exploded view of an apparatus according to one alternative embodiment of the invention.

Referring to FIG. 4, a caudal, exploded, perspective view illustrates another embodiment of the present invention. As shown, the inferior facet joint implants 40 and superior facet joint implants 58 of FIGS. 1-3 are once again present, with the vertebrae 24, 26 omitted for clarity. In place of the castle nuts 86, nuts 186 with a slightly different configuration may be applied to secure the implants 40, 58 to the vertebrae 24, 26, respectively. The inferior facet joint implants 40 may be secured together through the use of a crosslink 190, which is shown in exploded form.

The crosslink 190 may have two implant coupling components 192, two bolts 194, two rod coupling components 196, two nuts 198, and a rod 200. These components correspond in function to their counterparts 92, 94, 96, 98, 100 of FIGS. 1-3, but are configured somewhat differently.

More precisely, each of the implant coupling components 192 is configured to serve as a resilient member capable of facilitating assembly of the crosslink 190 enabling temporary attachment of the implant coupling components 192 to the inferior facet joint implants 40. Each implant coupling component 192 has a linking extension 220 shaped to grip the crosslink coupling feature 76 of the corresponding inferior facet joint implant 40. Each linking extension 220 includes an arm 221 that is bendable toward or away from the remainder of the linking extension 220. Each linking extension 220 defines a semicylindrical interface 222, at least a portion of which is provided by the arm 221. Each of the arms 221 has two prongs 223 that may curve outward slightly from the open portion of the semicylindrical interface 222 to facilitate sliding of the crosslink coupling feature 76 into the cavity provided by the semicylindrical interface 222.

Due to the resiliency of the arm 221, the semicylindrical interface 222 may be urged into a wider configuration to permit insertion of the corresponding crosslink coupling feature 76 through the open portion of the semicylindrical interface 222. Once the crosslink coupling feature 76 is within the hollow interior of the semicylindrical interface 222, the arm 221 is able to "snap" back to an undeflected or less deflected state to retain the crosslink coupling feature 76. In this application, "snapping into engagement" refers to deflection of a resilient member, followed by a return of the resilient member to an undeflected or less deflected state to provide at least temporary retention of another member. Once the implant coupling component 192 has snapped into engagement with the crosslink coupling feature 76, friction between the semicylindrical interface 222 and the semicylindrical interface 114 of the crosslink coupling feature 76 tends to resist relative motion between the inferior facet joint implant 40 and the crosslink coupling feature 192.

The clocking feature 164 of the crosslink coupling feature 76 may help to provide additional friction that tends to prevent relative rotation between the crosslink coupling feature 76 and the implant coupling component 192. However, since the grooves and ridges of the clocking feature 164 extend generally parallel to the axis of the semicylindrical interface 114, the clocking feature 164 may not significantly inhibit motion of the implant coupling component 192 along the axis of the crosslink coupling feature 76. Accordingly, after the linking extension 220 of the crosslink coupling component 192 has snapped into engagement with the crosslink coupling feature 76, the implant coupling component 192 may optionally still be repositionable relative to the crosslink coupling feature 76 along an axis extending generally along the cephalad/caudal direction. However, knurling, circumferential grooves, or other features may be used as an alternative to the clocking feature 164 to prevent such adjustability, if desired.

Each implant coupling component 192 also has a clocking feature 124 like that of the implant coupling component 92 of the previous embodiment. The clocking feature 124 may thus take the form of a plurality of radially arrayed grooves and/or ridges. The grooves and/or ridges may mesh with similar features on the opposing surface of the corresponding rod coupling component 196, as will be described subsequently.

The implant coupling component 192 also has a bore 226 through which the bolt 194 may be inserted to provide stronger and more rigid attachment of the implant coupling component 192 to the crosslink coupling feature 76. The manner in which stronger and more rigid attachment may be carried out will be set forth subsequently.

Each bolt 194 has a configuration similar to that of the bolts 94 of the previous embodiment. Each bolt 194 may have a head 230 and a shank 232 extending from the head 230. The shank 232 is threaded, and the head 230 has a gripping extension 234 that extends asymmetrically from the axis of the shank 232 to press against the crosslink coupling feature 76 when the bolt 194 is under tension. Upon insertion of the shank 232 through the bore 226, the gripping extension 234 fits between the prongs 223 of the arm 221 of the linking extension 220. Thus, the gripping extension 234 is able to press directly against the crosslink coupling feature 76 without interference from the arm 221.

Each rod coupling component 196 has a linking extension 240 designed to receive the corresponding end of the rod 200. Each linking extension 240 has a semicylindrical interface 242 that receives the rod 200 in a manner that permits slidable adjustment of the rod 200 within semicylindrical interface 242 until the rod 200 is locked in place with respect to the linking extension 240. Each rod coupling component 196 is substantially U-shaped, with the linking extension 240 as the curved portion of the U-shape. When the free ends of the U-shape are compressed, the rod coupling component 196 is compressed to decrease the radius of the semicylindrical interface 242, thereby gripping the rod 200 to prevent further sliding motion of the rod 200 within the semicylindrical interface 242.

As indicated previously, each rod coupling component 196 also has a clocking feature 244 that is similar in configuration to the clocking features 124 of the implant coupling components 192. Accordingly, each clocking feature 244 may have ridges and/or grooves in a radial arrangement that enables them to mesh with the ridges and/or grooves of the clocking feature 124. Thus, the clocking features 124, 244 may cooperate to limit the relative orientations of each rod coupling component 196 and its corresponding implant coupling component 192 to a discrete number of selections. Additionally, the clocking features 124, 244 cooperate to prevent rotational slippage between each rod coupling component 196 and its corresponding implant coupling component 192 when the crosslink 190 has been fully assembled and tightened.

Each rod coupling component 196 also has a bore 246 that receives the shank 232 of the bolt 194. Each bore 246 has a semispherical countersink 248 that receives the corresponding nut 198. Tightening the nut 198 on the bolt 194 compresses the free ends of the U-shape of the rod coupling component 196 together to grip the rod 200. The semispherical countersink 248 enables polyaxial rotation of the nut 198 relative to the rod coupling component 196 to maintain significant surface contact between the nut 198 and the rod coupling component 196 when the rod coupling component 196 compresses. This helps to prevent binding of the nut 198 as the bolt 194 and the nut 198 are tightened.

The nut 198 has a torque receiver 250 designed to interface with a torquing instrument (not shown) such as a hex driver. The torque receiver 250 has a corresponding shape such as a hexagonal shape. The nut 198 also has a semispherical surface 252 with a radius substantially the same as that of the semispherical countersink 248 of the bore 246 of the rod coupling component 196. Thus, the semispherical surface 252 fits into the semispherical countersink 248 and the surface contact between the nut 198 and the semispherical countersink 248 is maintained despite variations in relative orientation between the nut 198 and the semispherical countersink 248. The nut 198 has a bore 256 with threads that engage the threads of the shank 232 of the bolt 194 to permit the nut 198 to be advanced, or tightened, along the shank 232 by rotating it with the torquing instrument.

As shown, the rod 200 has a first end 260 and a second end 262. Each of the ends 260, 262 may have a clocking feature 264 designed to restrict relative rotation between the ends 260, 262 and the corresponding rod coupling components 196 and/or limit the relative orientations of the rod coupling components 196 to set of discrete angular offsets about the axis of the rod 200. Each clocking feature 264 may take the form of a plurality of grooves and/or ridges oriented parallel to the axis of the rod 200 and arrayed about the circumference of the corresponding end 260 or 262.

According to alternative embodiments, other types of clocking features may be used to confine the relative positions and/or orientations of the inferior facet joint implants 40 to discrete increments and/or reduce slippage in the tightened crosslink 190. If desired, circumferential grooves and ridges may be used in place of, or in addition to, the grooves and/or ridges of the clocking features 264 of FIG. 4. Such circumferential grooves and/or ridges may help to further resist slippage of the ends 260, 262 relative to their corresponding rod coupling components 196, and may limit the relative positions of the rod coupling components 196 along the rod 200 to discrete increments.

After exposure of the operating site, the implants 40, 58 and the crosslink 190 may be installed and assembled according to a wide variety of methods. According to one method, the operating site is first exposed and the implants 40, 58 are attached to the vertebrae 24, 26 in the desired positions and orientations. This attachment may be strong enough to keep the implants 40, 58 in place during assembly and attachment of the crosslink 190, but need not be strong enough to bear the loads associated with articulation of the implants 40, 58.

The crosslink 190 may then be loosely assembled and movably secured to the inferior facet joint implants 40. This may be accomplished by, first, mating the clocking features 124, 244 of the implant coupling component 192 and the rod coupling component 196 with each other, and then inserting the shank 232 of the bolt 194 through the aligned bores 226, 246 of the implant coupling component 192 and the rod coupling component 196. The nut 198 may then be inserted onto the exposed end of the shank 232 and rotated so that the threads of the bore 256 of the nut 198 engage those of the shank 232. The nut 198 is not, however, tightened into the semispherical countersink 248. Thus, relative rotation between the implant coupling component 192 and the rod coupling component 196 is still possible.

The ends 260, 262 of the rod 200 may then be inserted into the linking extensions 240 of the rod coupling components 196. Since the nuts 198 have not been tightened, the ends 260, 262 can still rotate and slide within the linking extensions 140. Thus, the implant coupling components 192 can move toward or away from each other, and can rotate relative to each other about two orthogonal axes. The implant coupling components 192 can therefore both be positioned to engage the crosslink coupling features 76 of their corresponding inferior facet joint implants 40 without disassembling the crosslink 190. The arms 221 of the linking extensions 220 of the implant coupling components 192 are deflected to push the crosslink coupling features 76 into the semicylindrical interfaces 222 of the linking extensions 220, and are then allowed to snap back to undeflected or less deflected configurations to provide temporary attachment of the crosslink 190 to the inferior facet joint implants 40.

The crosslink 190 is then attached to the inferior facet joint implants 40, but is still reconfigurable and adjustable. The implant coupling components 192 can slide along the crosslink coupling features 76 to permit cephalad/caudal adjustment of the position of the crosslink 190 to most effectively avoid interference with portions of the spine 10, such as the spinous process 36 of the first vertebra 24. Furthermore, if reorientation of the inferior facet joint implants 40 is needed, this can be carried out without detaching the crosslink 190.

Once the inferior facet joint implants 40 and the crosslink 190 have been positioned as desired, the torquing instrument (not shown) may be used to tighten the nuts 198 so that they press into the semispherical countersinks 248. If desired, the torquing instrument may be used to tighten the nuts 198 to a predefined torque. The torquing instrument may optionally be designed to be capable of applying only the appropriate maximum torque to the nuts 198.

Tightening the nuts 198 also advances the gripping extension 234 of each bolt 194 toward the facing portion of the corresponding semicylindrical interface 222 to securely retain the corresponding crosslink coupling feature 76 between the prongs 223 of the associated arm 221. Additionally, tightening the nuts 198 compresses and deflects the rod coupling components 192 to cause the semicylindrical interfaces 242 to grip the ends 260, 262 of the rod 200. Furthermore, tightening the nuts 198 causes the clocking features 124, 244 of the implant coupling components 192 and the rod coupling components 196 to tightly engage each other to prevent relative rotation between the implant coupling components 192 and the rod coupling components 196. Hence, tightening the nuts 198 locks the crosslink 190 to prevent at least three different modes of relative motion between the inferior facet joint implants 40. Advantageously, no other fastening elements need be tightened to place the crosslink 190 in a rigid configuration.

Figure 5:
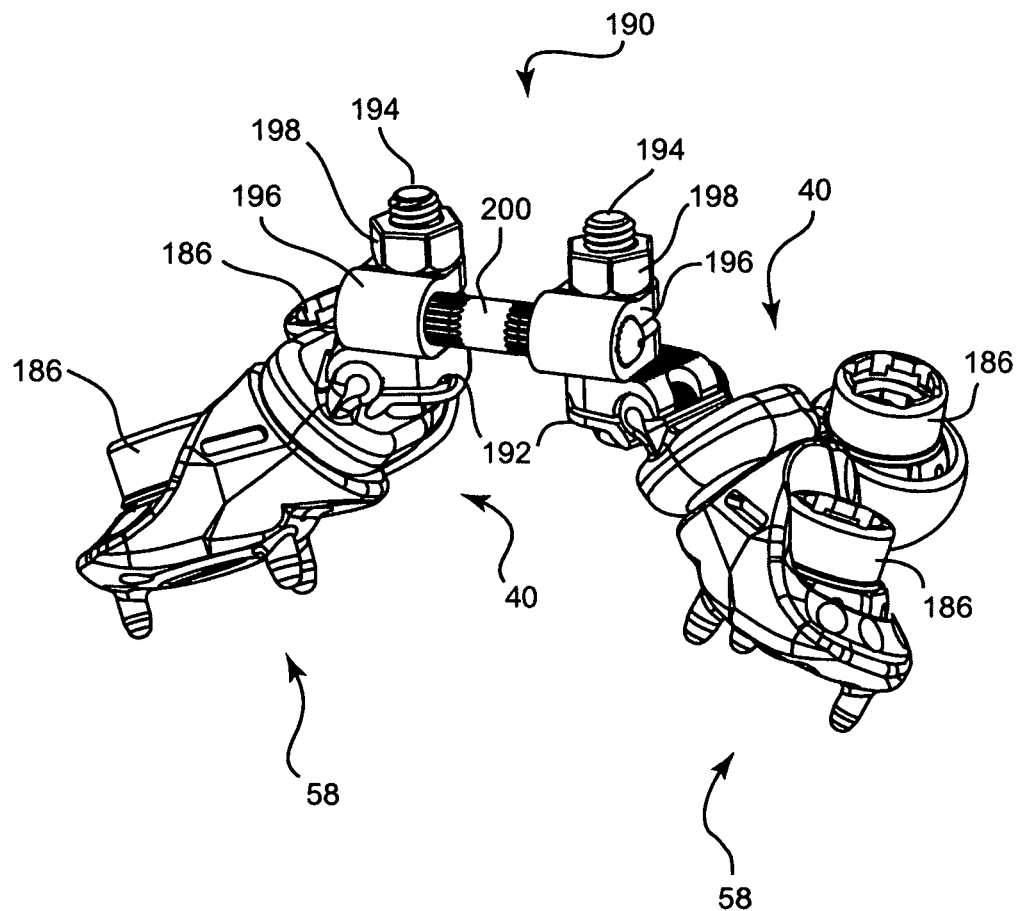
FIG. 5 is a caudal, perspective view of the apparatus of FIG. 4, in a fully assembled configuration.

Referring to FIG. 5, the implants 40, 58 and the crosslink 190 are illustrated in a fully assembled and tightened state. The implants 40, 58 and the crosslink 190 are fully installed and ready for use. The surgical site may then be closed according to known methods. If revision surgery is ever needed, the nuts 198 may easily be loosened to permit reconfiguration of the crosslink 190 and reorientation of the inferior facet joint implants 40.

Notably, the rod coupling components 196 may be attached to the implant coupling components 192 in two different ways. FIG. 5 illustrates the positioning of the rod 200 caudal to the bolts 194. This mode of assembly may normally be most desirable to avoid interference and/or contact with the spinous process 36 of the first vertebra 24. However, in the event that the spinous process 36 has been resected or naturally has a less extensive caudal dimension, the rod coupling components 196 may be rotated 180° from the orientation shown in FIG. 5 so that the rod 200 is cephalad to the bolts 194. Such a configuration may help to avoid interference with spinal anatomy caudal to the crosslink 190.

Although the foregoing description focuses on crosslinking of facet joint replacement implants, those of skill in the art will recognize that the principles taught herein could be applied to a wide variety of orthopedic implants. The present invention may be particularly useful for bilateral implants that are placed close enough together to permit crosslinking.

The present invention may be embodied in other specific forms without departing from its spirit or essential characteristics. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system comprising:
a first left implant having an opening for receiving a first fastener, the first fastener having a first head portion and first shaft portion, the first shaft portion engageable with a first vertebra, the first left implant comprising a first left articular surface and a left crosslink coupling interface, wherein the first left articular surface is shaped to articulate with a second left articular surface on a second vertebra;
a first right implant having an opening for receiving a second fastener, the second fastener having a second head portion and second shaft portion, the second shaft portion engageable with the first vertebra, the first right implant comprising a first right articular surface shaped to articulate with a second right articular surface on the second vertebra; and
a crosslink attachable to the first left and right implants to secure the first left implant with respect to the first right implant at any of a limited number of discrete relative displacements, the crosslink comprising a rod and a left implant coupling component, wherein the rod attaches to the left implant coupling component, the left implant coupling component having a left implant coupling interface, wherein the left implant coupling interface attaches directly to the left crosslink coupling interface, wherein a left clocking feature including a plurality of ridges facing the crosslink formed between the left implant coupling interface and the left crosslink coupling interface, wherein the left clocking feature limits attachment between the left implant coupling component and the first left implant to the discrete relative displacements,
wherein the left implant coupling component comprises a resilient member, wherein the resilient member comprises the left implant coupling interface, wherein the left implant coupling interface snaps onto the left crosslink coupling interface to secure the first left implant to the first right implant.

2. The system of claim 1, wherein the crosslink comprises a right implant coupling component, wherein the left and right implant coupling components are securable to the first left and right implants, respectively, independently of securing the first left implant to the first right implant.

3. The system of claim 1, wherein the crosslink is adjustably positionable with respect to the first left implant along an axis having a substantially cephalad/caudal orientation.

4. The system of claim 1, wherein the discrete relative displacements are rotationally offset from each other.

5. The system of claim 1, wherein the crosslink is configured such that attachment of the crosslink to the first left and right implants does not place the crosslink in direct contact with the first vertebra.

6. The system of claim 1, wherein the crosslink is configured such that attachment of the crosslink to the first left and right implants does not require resection of a spinous process of the first vertebra.

7. The system of claim 1, wherein the crosslink further comprises a right implant coupling component, wherein the left and right implant coupling components are securable to the first left and right implants, respectively, wherein the rod is attachable to the left and right implant coupling components to secure the left and right implant coupling components together at any of a plurality of displacements of the right implant coupling component with respect to the left implant coupling component.

8. The system of claim 7, wherein the crosslink further comprises a left rod coupling component attachable directly to the rod and the left implant coupling component, wherein at least one of the left implant coupling component and the left rod coupling component comprises a clocking feature configured to limit attachment between the left rod coupling component and the left implant coupling component to the discrete relative displacements.

9. A system comprising:
a first left implant attachable to a first vertebra, the first left implant comprising a first left articular surface;
a second left implant attachable to a second vertebra, the second left implant comprising a second left articular surface, wherein the first left articular surface is shaped to articulate with the second left articular surface on the second left implant;
a first right implant attachable to the first vertebra, the first right implant comprising a first right articular surface;
a second right implant attachable to the second vertebra, the second right implant comprising a second right articular surface, wherein the first right articular surface is shaped to articulate with the second right articular surface on the second right implant; and
a crosslink attachable to the first left and right implants, the crosslink comprising a left resilient member that engages the first left implant and a right resilient member that engages the first right implant, the left and right resilient members adjustably arranged on a rod of the crosslink, wherein, when the crosslink is attached to the first left and right implants, the first left implant and first right implant are adjustably positionable relative to each other in a medial/lateral direction,
a clocking feature positioned between the first left implant and the crosslink, the clocking feature including a plurality of ridges facing the crosslink, wherein the clocking feature restricts rotation between the first left implant and the crosslink, wherein each of the left and right resilient members comprises an implant coupling interface that engages a corresponding crosslink coupling interface on a corresponding one of the first left and right implants,
wherein each crosslink coupling interface comprises a semicylindrical protrusion and the implant coupling interface comprises a semicylindrical cavity that is expandable to receive the semicylindrical protrusion.

10. The system of claim 9, wherein each of the left and right resilient members comprises a monolithic clip having a stationary arm and a bendable arm, wherein the bendable arm is configured to bend relative to the stationary arm to permit each resilient member to receive and grip a corresponding crosslink coupling interface on a corresponding one of the first left and right implants.

11. The system of claim 9, further comprising a fastener configured to be actuated independently of engaging each of the left and right resilient members into engagement to substantially prevent disengagement of each resilient member.

12. A system comprising:
a first left implant having an opening for receiving a first fastener, the first fastener having a first head portion and first shaft portion, the first shaft portion engageable with a first vertebra, the first left implant comprising a first left articular surface and a left crosslink coupling interface, wherein the first left articular surface is shaped to articulate with a second left articular surface on a second vertebra;
a first right implant having an opening for receiving a second fastener, the second fastener having a second head portion and second shaft portion, the second shaft portion engageable with the first vertebra, the first right implant comprising a first right articular surface and a right crosslink coupling interface, wherein the first right articular surface is shaped to articulate with a second right articular surface on the second vertebra;
a crosslink comprising a rod, a left implant coupling component attachable to a first end of the rod, and a right implant coupling component attachable to a second end of the rod opposite the first end, wherein the left implant coupling component comprises a left implant coupling interface, wherein the right implant coupling component comprises a right implant coupling interface, wherein the left and right coupling interfaces interlock with the left and right crosslink coupling interfaces, respectively, independently of attaching the rod to the left and right implant coupling components and independently of securing the first left implant to the first right implant; and
a clocking feature including a plurality of ridges facing the crosslink formed between the left implant coupling interface and the left crosslink coupling interface, wherein the clocking feature restricts relative rotation between the left implant coupling interface and the left crosslink coupling interface,
wherein the left implant coupling component comprises a resilient member, wherein the resilient member comprises the left implant coupling interface, wherein the left implant coupling interface snaps onto the left crosslink coupling interface to secure the first left implant to the first right implant.

13. The system of claim 12, wherein the rod attaches to the left and right implant coupling components to secure the left and right implant coupling components together at any of a plurality of displacements of the right implant coupling component with respect to the left implant coupling component.

14. The system of claim 13, wherein the crosslink further comprises a left rod coupling component attachable directly to the rod and the left implant coupling component.

15. The system of claim 14, wherein the left rod coupling component is attachable at a variety of relative orientations with respect to the left implant coupling component and at a variety of relative orientations with respect to the rod.

16. A system comprising:
a first left implant having an opening for receiving a first fastener, the first fastener having a first head portion and first shaft portion, the first shaft portion engageable with a first vertebra, the first left implant comprising an implant stem, a first left articular surface, and a left crosslink coupling interface, wherein the first left articular surface is shaped to articulate with a second left articular surface on a second vertebra;
a first right implant having an opening for receiving a second fastener, the second fastener having a second head portion and second shaft portion, the second shaft portion engageable with the first vertebra, the first right implant comprising a first right articular surface shaped to articulate with a second right articular surface on the second vertebra; and
a crosslink attachable to secure the first left implant to the first right implant, the crosslink comprising a rod and a left implant coupling component, wherein the rod attaches to the left implant coupling component, the left implant coupling component comprising a left implant coupling interface, wherein the left implant coupling interface attaches directly to the left crosslink coupling interface, wherein a left clocking feature is formed between the left implant coupling interface and the left crosslink coupling interface, wherein the crosslink is adjustably positionable with respect to the first left implant along a first axis having a substantially cephalad/caudal orientation, wherein the first axis is displaced from a second axis defined by the implant stem in at least one of an angular displacement and a linear displacement; and
wherein the left a clocking feature includes a plurality of ridges facing the crosslink wherein the left clocking feature restricts relative rotation between the left implant coupling interface and the left crosslink coupling interface,
wherein the left crosslink coupling interface comprises a shape that is generally elongated along the first axis to permit attachment of the left implant coupling interface at any of a plurality of positions along the left crosslink coupling interface,
wherein the left crosslink coupling interface comprises a semicylindrical protrusion and the left implant coupling interface comprises a semicylindrical cavity sized to receive the semicylindrical protrusion.

17. A method comprising:
positioning a first left articular surface of a first left implant to articulate with a second left articular surface on a second vertebra, the first left implant comprising an opening for receiving a first fastener and a left crosslink coupling interface;
attaching the first left implant to the first vertebra using the first fastener, the first fastener having a first head portion and first shaft portion, the first shaft portion engaging the first vertebra;
positioning a first right articular surface of a first right implant to articulate with a second right articular surface on the second vertebra;

attaching the first right implant to the first vertebra using a second fastener, the second fastener having a second head portion and second shaft portion, the second shaft portion engaging the second vertebra; and attaching a crosslink to the first left and right implants to secure the first left implant with respect to the first right implant at any of a limited number of discrete relative displacements, the crosslink comprising a rod and a left implant coupling component, the left implant coupling interface comprising a left implant coupling interface, and wherein a left clocking feature includes a plurality of ridges facing the crosslink, wherein the left clocking feature restricts relative rotation between the left implant coupling interface and the left crosslink coupling interface;

wherein the left clocking feature is formed between the left implant coupling interface and the left crosslink coupling interface, wherein the left clocking feature limits attachment between the left implant coupling component and the first left implant to the discrete relative displacements;

wherein attaching the crosslink to the first left and right implants comprises attaching the rod to the left implant coupling component and attaching the left implant coupling interface directly to the left crosslink coupling interface, wherein the left implant coupling component comprises a resilient member, wherein the resilient member comprises the left implant coupling interface, wherein attaching the crosslink to the first left and right implants comprises snapping the left implant coupling interface into engagement with the left crosslink coupling interface.

18. The method of claim 17, wherein the crosslink comprises a right implant coupling component, wherein attaching the crosslink to the first left and right implants comprises securing the left and right implant coupling components to the first left and right implants, respectively, independently of securing the first left implant to the first right implant.

19. The method of claim 17, wherein attaching the crosslink to the first left and right implants comprises adjusting a position of the crosslink with respect to the first left implant along an axis having a substantially cephalad/caudal orientation.

20. The method of claim 17, wherein the discrete relative displacements are rotationally offset from each other.

21. The method of claim 17, wherein attaching the crosslink to the first left and right implants comprises positioning the crosslink to avoid direct contact with the first vertebra.

22. The method of claim 17, wherein attaching the crosslink to the first left and right implants comprises positioning the crosslink to avoid requiring resection of a spinous process of the first vertebra.

23. The method of claim 17, wherein the crosslink further comprises a right implant coupling component, wherein attaching the crosslink to the first left and right implants comprises:
 securing the left implant coupling component to the first left implant;
 securing the right implant coupling component to the first right implant; and
 attaching the rod to the left and right implant coupling components to secure the left and right implant coupling components together at any of a plurality of displacements of the right implant coupling component with respect to the left implant coupling component.

24. The method of claim 23, wherein the crosslink further comprises a left rod coupling component attachable directly to the rod and the left implant coupling component, wherein attaching the crosslink to the first left and right implants further comprises limiting attachment between the left rod coupling component and the left implant coupling component to the discrete relative displacements.

25. A method comprising:
 positioning a first left articular surface of a first left implant to articulate with a second left articular surface on a second vertebra;
 attaching the first left implant to a first vertebra using a first fastener, the first fastener having a first head portion and first shaft portion, the first shaft portion engaging the first vertebra, the first left implant having an opening for receiving the first fastener;
 positioning a first right articular surface of a first right implant to articulate with a second right articular surface on the second vertebra;
 attaching the first right implant to the first vertebra using a second fastener, the second fastener having a second head portion and second shaft portion, the second shaft portion engaging the second vertebra the first right implant having an opening for receiving the second fastener; and
 securing the first right implant to the first left implant through the use of a crosslink;
 wherein a clocking feature is positioned between the first left implant and the crosslink, the clocking feature including a plurality of ridges facing the crosslink, wherein the clocking feature restricts rotation between the first left implant and the crosslink;
 wherein securing the first right implant to the first left implant comprises engaging a left resilient member of the crosslink onto the first left implant and engaging a right resilient member of the crosslink onto the first right implant, the left and right resilient members adjustably arranged on a rod of the crosslink,
 wherein, after securing the first right implant to the first left implant, the first left implant and first right implant are adjustably positionable relative to each other along at least a medial/lateral axis,
 wherein engaging the left resilient member onto the first left implant comprises snapping an implant coupling interface of the left resilient member into direct engagement with a corresponding crosslink coupling interface on the first left implant.

26. The method of claim 25, wherein the crosslink coupling interface comprises a semicylindrical protrusion and the implant coupling interface comprises a semicylindrical cavity, wherein snapping the implant coupling interface into engagement with the corresponding crosslink coupling interface comprises expanding the semicylindrical cavity to receive the semicylindrical protrusion.

27. The method of claim 25, wherein each of the left and right resilient members comprises a monolithic clip having a stationary arm and a bendable arm, wherein engaging each resilient member onto a corresponding one of the first left and right implants comprises bending the bendable arm relative to the stationary arm to permit each resilient member to receive and grip a corresponding crosslink coupling interface on the corresponding implant.

28. The method of claim 25, wherein securing the first right implant to the first left implant further comprises actuating a fastener independently of engaging the resilient member into engagement to substantially prevent disengagement of the resilient member.

29. A method comprising:
- positioning a first left articular surface of a first left implant to articulate with a second left articular surface on a second vertebra, the first left implant comprising a left crosslink coupling interface;
- attaching the first left implant to a first vertebra using a first fastener, the first fastener having a first head portion and first shaft portion, the first shaft portion engaging the first vertebra, the first left implant having an opening for receiving the first fastener;
- positioning a first right articular surface of a first right implant to articulate with a second right articular surface on the second vertebra, the first right implant comprising a right crosslink coupling interface;
- attaching the first right implant to the first vertebra using a second fastener, the second fastener having a second head portion and second shaft portion, the second shaft portion engaging the first vertebra, the first right implant having an opening for receiving the second fastener;
- securing a left implant coupling interface of a left implant coupling component of a crosslink with the left crosslink coupling interface of the first left implant;
- wherein a clocking feature is positioned between the left implant coupling component and the left crosslink coupling interface, the clocking feature including a plurality of ridges facing the crosslink, wherein the clocking feature restricts rotation between the left implant coupling component and the left crosslink coupling interface;
- securing the right implant coupling interface of a right implant coupling component of the crosslink with a right crosslink coupling interface of the first right implant;
- securing the first right implant to the first left implant through the use of a first end of a rod of the crosslink to the left implant coupling component; and
- securing a second end of the rod to the right implant coupling component, wherein the second end of the rod is opposite the first end of the rod;
- wherein securing the rod to the left and right implant coupling components is independent of securing the first left implant to the first right implant,
- wherein the left implant coupling component comprises a resilient member, wherein the resilient member comprises the left implant coupling interface, wherein attaching the crosslink to the first left and right implants comprises snapping the left implant coupling interface into engagement with the left crosslink coupling interface.

30. The method of claim 29, wherein securing the rod to the left and right implant coupling components comprises attaching the rod of the crosslink to the left and right implant coupling components at any of a plurality of displacements of the right implant coupling component with respect to the left implant coupling component.

31. The method of claim 30, wherein securing the first right implant to the first left implant further comprises attaching a left rod coupling component directly to the rod and the left implant coupling component.

32. The method of claim 31, wherein attaching a left rod coupling component directly to the rod and the left implant coupling component comprises:
- attaching the left rod coupling component to the left implant coupling component at any of a variety of relative orientations; and
- attaching the left rod coupling component to the rod at any of a variety of relative orientations.

33. A method comprising:
- positioning a first left articular surface of a first left implant to articulate with a second left articular surface on a second vertebra;
- attaching the first left implant to the first vertebra, wherein the first left implant further comprises an implant stem and a left crosslink coupling interface;
- positioning a first right articular surface of a first right implant to articulate with a second right articular surface on the second vertebra;
- attaching the first right implant to the first vertebra using a fastener, the fastener having a head portion and shaft portion, the shaft portion engaging the first vertebra, the first right implant having an opening for receiving the fastener;
- adjustably positioning a crosslink with respect to the first left implant along a first axis having a substantially cephalad/caudal orientation, wherein the first axis is displaced from a second axis defined by the implant stem in at least one of an angular displacement and a linear displacement, the crosslink comprising a rod and a left implant coupling component, wherein the rod attaches to the left implant coupling component, the left implant coupling component comprising a left implant coupling interface;
- wherein a left clocking feature is formed on at least one of the left implant coupling interface and the left crosslink coupling interface; and
- securing the first right implant to the first left implant through the use of the crosslink,
- wherein securing the first right implant to the first left implant comprises attaching the left implant coupling interface of the crosslink to the left crosslink coupling interface of the first left implant, wherein the left crosslink coupling interface comprises a shape that is generally elongated along the first axis; wherein attaching the left implant coupling interface to the left crosslink coupling interface comprises attaching the left implant coupling interface at any of a plurality of positions along the left crosslink coupling interface,
- wherein the left crosslink coupling interface comprises a semicylindrical protrusion and the left implant coupling interface comprises a semicylindrical cavity, wherein attaching the left implant coupling interface to the left crosslink coupling interface comprises a receiving the semicylindrical protrusion in the semicylindrical cavity.

* * * * *